United States Patent [19]

Stutman et al.

[11] Patent Number: 5,576,952
[45] Date of Patent: *Nov. 19, 1996

[54] MEDICAL ALERT DISTRIBUTION SYSTEM WITH SELECTIVE FILTERING OF MEDICAL INFORMATION

[75] Inventors: Peter S. Stutman, Sudbury; J. Mark Miller, Belmont, both of Mass.

[73] Assignee: Metriplex, Inc., Mass.

[ * ] Notice: The term of this patent shall not extend beyond the expiration date of Pat. No. 5,416,695.

[21] Appl. No.: 28,333

[22] Filed: Mar. 9, 1993

[51] Int. Cl.⁶ .............................. G06F 17/30; G06F 17/00
[52] U.S. Cl. ................... 364/413.02; 128/670; 128/700; 128/702; 364/413.03; 364/DIG. 1; 379/38; 395/200.03
[58] Field of Search ..................................... 395/600, 148, 395/161, 575; 128/710, 677, 670, 702; 364/413.02, 413.03; 379/38

[56] References Cited

U.S. PATENT DOCUMENTS

| | | | |
|---|---|---|---|
| 4,486,853 | 12/1984 | Parsons | 395/118 |
| 4,674,044 | 6/1987 | Kalmus et al. | 364/408 |
| 4,823,265 | 4/1989 | Nelson | 364/408 |
| 4,868,866 | 10/1989 | Williams | 380/49 |
| 4,974,607 | 4/1990 | Miwa | 128/904 |
| 5,003,473 | 3/1991 | Richards | 364/408 |
| 5,007,429 | 4/1991 | Treatch et al. | 364/413.03 |
| 5,012,411 | 4/1991 | Policastro et al. | 364/413.06 |
| 5,086,391 | 2/1992 | Chambers | 364/413.02 |
| 5,111,384 | 5/1992 | Aslanian et al. | 395/575 |
| 5,199,439 | 4/1993 | Zimmerman et al. | 128/670 |
| 5,247,611 | 9/1993 | Norden-Paul et al. | 395/161 |
| 5,253,361 | 10/1993 | Thurman et al. | 395/600 |
| 5,253,362 | 10/1993 | Nolan et al. | 395/600 |
| 5,301,319 | 4/1994 | Thurman et al. | 395/600 |
| 5,325,478 | 6/1994 | Shelton et al. | 395/600 |
| 5,474,090 | 1/1989 | Begun et al. | 128/707 |

FOREIGN PATENT DOCUMENTS

| | | |
|---|---|---|
| 0505627 | 9/1992 | European Pat. Off. . |
| 3815633 | 3/1989 | Germany . |
| 4056561 | 2/1992 | Japan . |

OTHER PUBLICATIONS

Article entitled, "Stock Quotes Join Mozart on FM", Information Processing, Business Week, Dec. 13, 1982.

Primary Examiner—Wayne Amsbury
Assistant Examiner—Hosain T. Alam
Attorney, Agent, or Firm—Cesari & McKenna

[57] ABSTRACT

The present invention relates to a medical alert distribution system which receives medical information (e.g. blood pressure, blood chemistry test results, etc.) from monitoring units worn by ambulatory patients. The system also receives medical selection and limit parameters from remote system subscriber units (e.g., a unit accessed by a doctor). The system repeatedly compares the medical information received form the ambulatory patients to determine if a selected parameter, as indicated by an asserted in-alert flag, has exceeded the limit parameters received form the remote subscriber units. If exceeded, the system sends a message (e.g., via a wireless paging message) to the system subscriber unit(s) which requested that the particular parameter be continuously compared against the selected limit parameters. Thus, the system selectively filters information and distributes filtered information to a subscriber processing unit by way of communications network.

13 Claims, 15 Drawing Sheets

MEDICAL ALERT DISTRIBUTION SYSTEM WITH SELECTIVE FILTERING OF MEDICAL INFORMATION

CROSS-REFERENCE TO RELATED APPLICATION

This invention is related to U.S. patent applications Ser. No. 08/028,351, now U.S. Pat. No. 5,416,695 issued to Stutman et al, titled METHOD AND APPARATUS FOR ALERTING MEDICAL PERSONNEL OF EMERGENCY MEDICAL CONDITIONS, and Ser. No. 08/028,356, titled REMOTE LIMIT-SETTING INFORMATION DISTRIBUTION SYSTEM, each filed Mar. 9, 1993 and each assigned to the assignee of the present invention.

FIELD OF THE INVENTION

This invention relates generally to information retrieval and distribution systems and, more specifically, to a medical alert distribution system.

BACKGROUND OF THE INVENTION

Information retrieval and distribution systems are typically characterized by the efficiency with which they can retrieve, update and distribute large amounts of information to authorized subscribers in real time. These systems are commonly used in financial and securities market applications where data acquisition and distribution techniques permit each subscriber to access only the type of information for which it is authorized.

What is needed is an information and distribution system of the type discussed above, but for medical information applications. Such an information system should have the ability to collect medical information from both stationary and mobile sources, the latter being ambulatory patients. For the latter case, the system should have the capability to detect the geographic location of the patient. Moreover, the system should allow authorized subscribers, such as health care givers, to enter limits and conditions from a remote location, and have those limits and conditions operate on the collected information and report back the results to the health care givers.

SUMMARY OF THE INVENTION

The invention resides in a medical alert distribution system for selectively filtering information at a host computer prior to distributing the filtered information to a remote processing device or "subscriber" by way of a communications network. The information may be stored in a database residing in a subsystem of an independent device that is coupled to the host computer or it may be contained in a database subsystem within the host computer; alternatively, the information may be provided directly to the host computer from a source by way of high-speed streams of data or by data packets.

Software modules resident in a "limit" software subsystem of the host computer are organized to interface with software modules resident in the database subsystem to selectively filter the information in response to selection and limit parameters provided by an authorized user of the subscriber. The software modules of the limit and database subsystems embody a plurality of independent processes, each of which perform specific operations.

In an exemplary embodiment of the invention, a "database" software process maintains a primary database of information records received from the sources and transfers the contents of the records to other processes upon request. Each database record includes an alert flag which, when asserted, directs the database process to transfer the contents of the record to an "alert" process of the limit subsystem.

The alert process maintains its own database of "alert records". In one embodiment of the invention, each alert record includes a selection parameter and "initial" and "incremental" limit parameters; however, in the exemplary embodiment, the alert record also includes a "high" limit parameter as provided by the subscriber. When the contents of a record are received in response to an asserted alert flag, the second process compares the received contents with a specific limit of its records and if a match occurs, the subscriber is notified of the condition, preferably by paging transmission. For example, the record contents are compared with the initial limit and, upon a match condition, the second process updates the initial limit parameter with the incremental limit. This updated parameter is compared with the contents of records subsequently received by the alert process and the subscriber is again notified of a sailsifted limit condition.

One advantage provided by this arrangement involves the dynamic filtering of information at a host computer. That is, the inbound information feeds, which are typically high-speed streams of data or data packets transmitted either directly to the host computer or to an intervening database subsystem, are manipulated at the host computer in accordance with selection and limit parameters provided by a remote subscriber device. This obviates the need for expensive hardware and software components to power and outfit the subscriber's device.

Another advantage of the system is that the software modules of the database subsystem and limit subsystem are organized as a plurality of independent processes with each process configured to perform specific operations. Some of these operations require more time to complete than others. Accordingly, the arrangement of independent processes allows efficient operation of the alert distribution system because the processes may perform their functions in parallel within the host computer or on separate machines having additional resources.

BRIEF DESCRIPTION OF THE DRAWINGS

The above and further advantages of the invention may be better understood by referring to the following description in conjunction with the accompanying drawings, in which.

DETAILED DESCRIPTION OF ILLUSTRATIVE EMBODIMENTS

Figure 1:
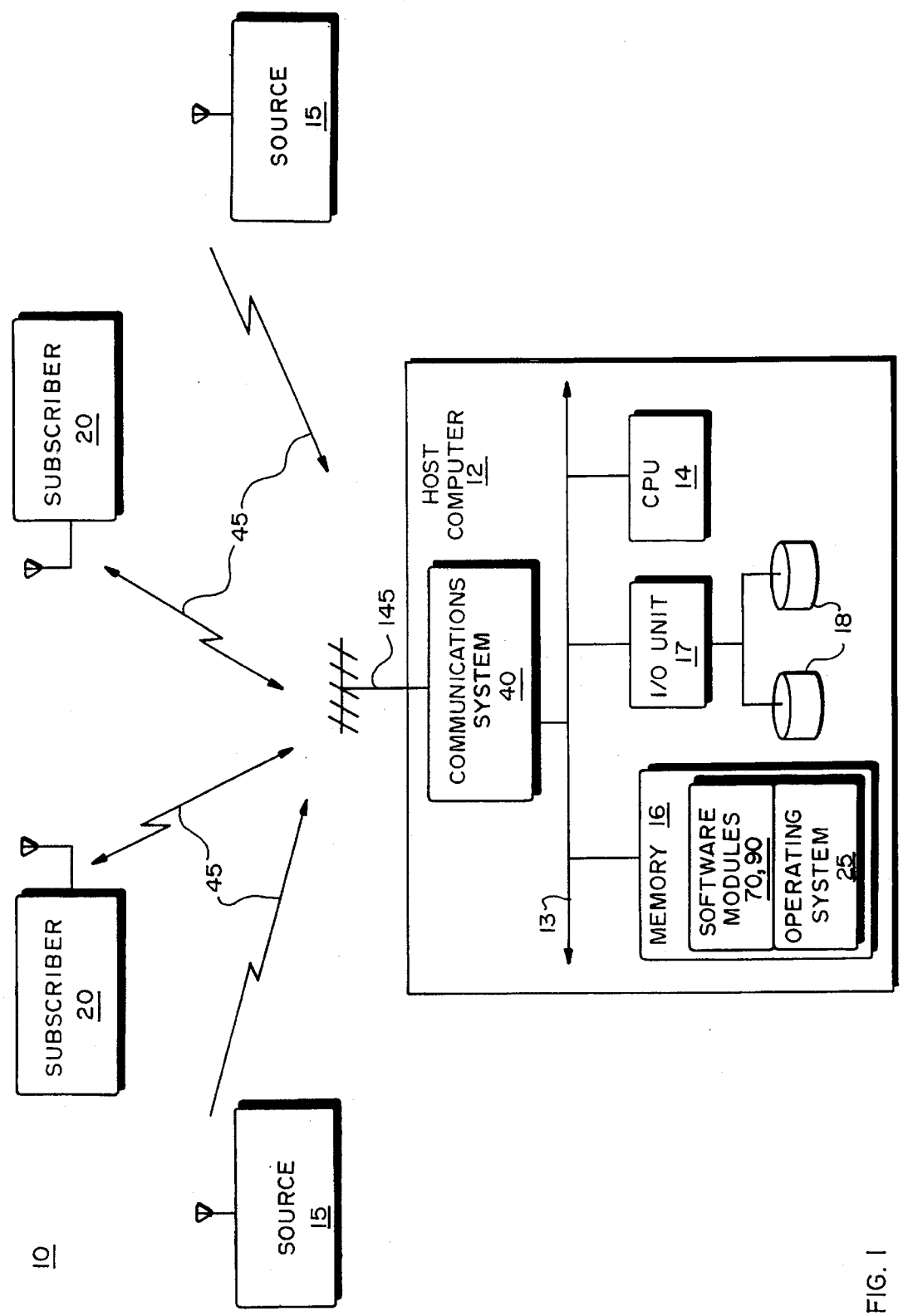
FIG. 1 is a diagram of a remotely-configurable medical alert distribution system comprising a plurality of information sources and subscriber units coupled to a host computer.

FIG. 1 depicts a medical alert distribution system 10 that includes a host computer 12 connected to a plurality of sources 15 and subscriber units 20. The host computer 12 is preferably configured to perform functions that typically involve frequent accesses to secondary storage media and, for the exemplary embodiment described herein, incorporates a database for storing the information received from the sources 15. However, in an alternate embodiment of the invention, the database may reside on another machine that is coupled to the host 12. The sources 15 collect medical information pertaining to the health of various patients and geodetic information pertaining to their locations, and supply that information to the host computer. The subscriber units 20 are typically processing devices such as intelligent terminals and portable computers. The subscribers and sources are coupled to a communications system 30 of the host via a network 45 which may include wireless radio communication or wireline (telephone line) connections.

The host computer 12 includes a central processing unit (CPU 14), an I/O unit 17 and associated storage devices 18, such as magnetic disks and tape drives, a main memory 16 and the communications system 30 interconnected by a system bus 13. An operating system 25, portions of which are typically resident in main memory 16 and executed by the CPU 14, functionally organizes the computer. The operating system 25 also includes, inter alia, software modules 110 (FIG. 4) executed by the communications system 30 to control the transfer of information to the other components of the computer 12. These modules are, in turn, responsible for invoking operations in support of application programs executing in the computer.

For the exemplary embodiment disclosed herein, the application programs pertain to real-time data acquisition and transactional processing. Such applications require fast data access to and from storage devices 18 that are shared among the subscribers 20 and sources 15. Instances of the software modules and application programs executing in the computer are called "processes". A process is an individually schedulable entity consisting of code and data, and characterized by dynamic states, as described below. The operating system 25 organizes the host computer 12 by tracking, suspending and resuming execution of the processes, while allocating to them the CPU 14 and other system resources.

The hardware and software components of the host computer 12 arrange related data items, i.e., records, into files and then organize the files in a manner that facilitates efficient and accurate inquiry and update. Specifically, host-based software modules 70, 90 resident in the memory 16 operate to selectively extract, i.e., "filter", the contents of the files in response to selection and limit parameters remotely provided by the subscribers 20, thereby enabling efficient performance of the data acquisition and transactional processing operations that characterize the computer.

Figure 2:
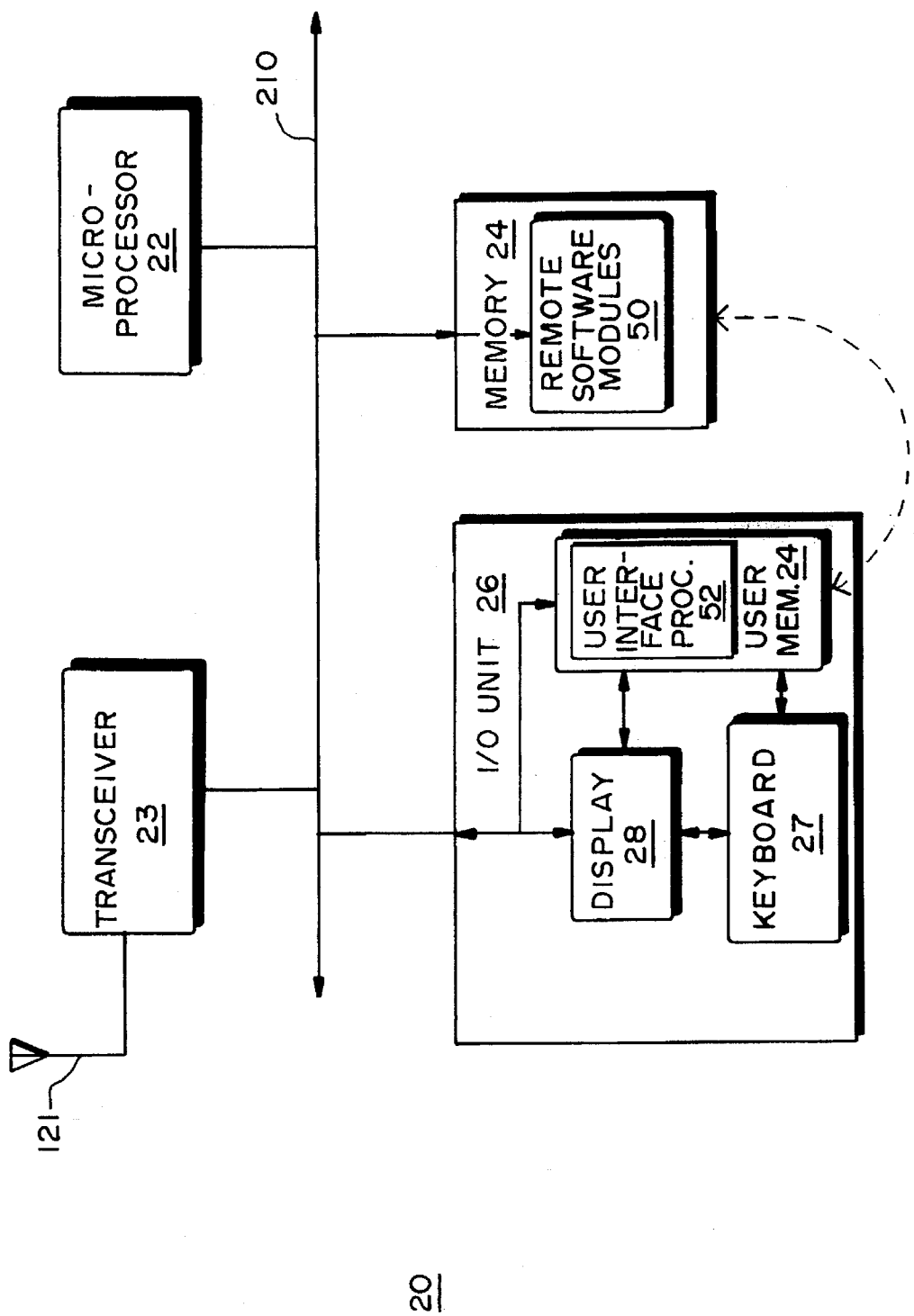
FIG. 2 is a block diagram of a subscriber unit.

The subscriber unit 20 comprises a microprocessor 22, a memory 24 and an I/O unit 26 interconnected by a bus 210, as shown in FIG. 2. Buffering of selection and limit parameters in the memory 24 and subsequent transfer of these parameters to the host computer 12 are controlled by the microprocessor 22. Remote software modules 50, typically resident in the memory 24, facilitate interpretation and organization of the selection and limit parameters entered by an authorized user.

As described further herein, a user interface process 52 of the remote software modules 50 presents a series of menus on a flat screen display 28 and provides for manipulation by a keyboard 27. The menus allow a user to enter the selection and limit parameters in a user-recognizable format, where translations are performed locally by the microprocessor 22 during execution of the software modules 50 prior to arranging the parameters in a message or "data packet" format. The microprocessor 22 then transfers the data packet to a transceiver unit 23 and the packet is transmitted over the network 45 to the host computer 12. For upload transmission of the packet to the host over a wireline medium, the transceiver unit 23 preferably comprises a wireline modem circuit configured to transmit the packet in accordance with conventional packet transfer protocols.

Figure 3:
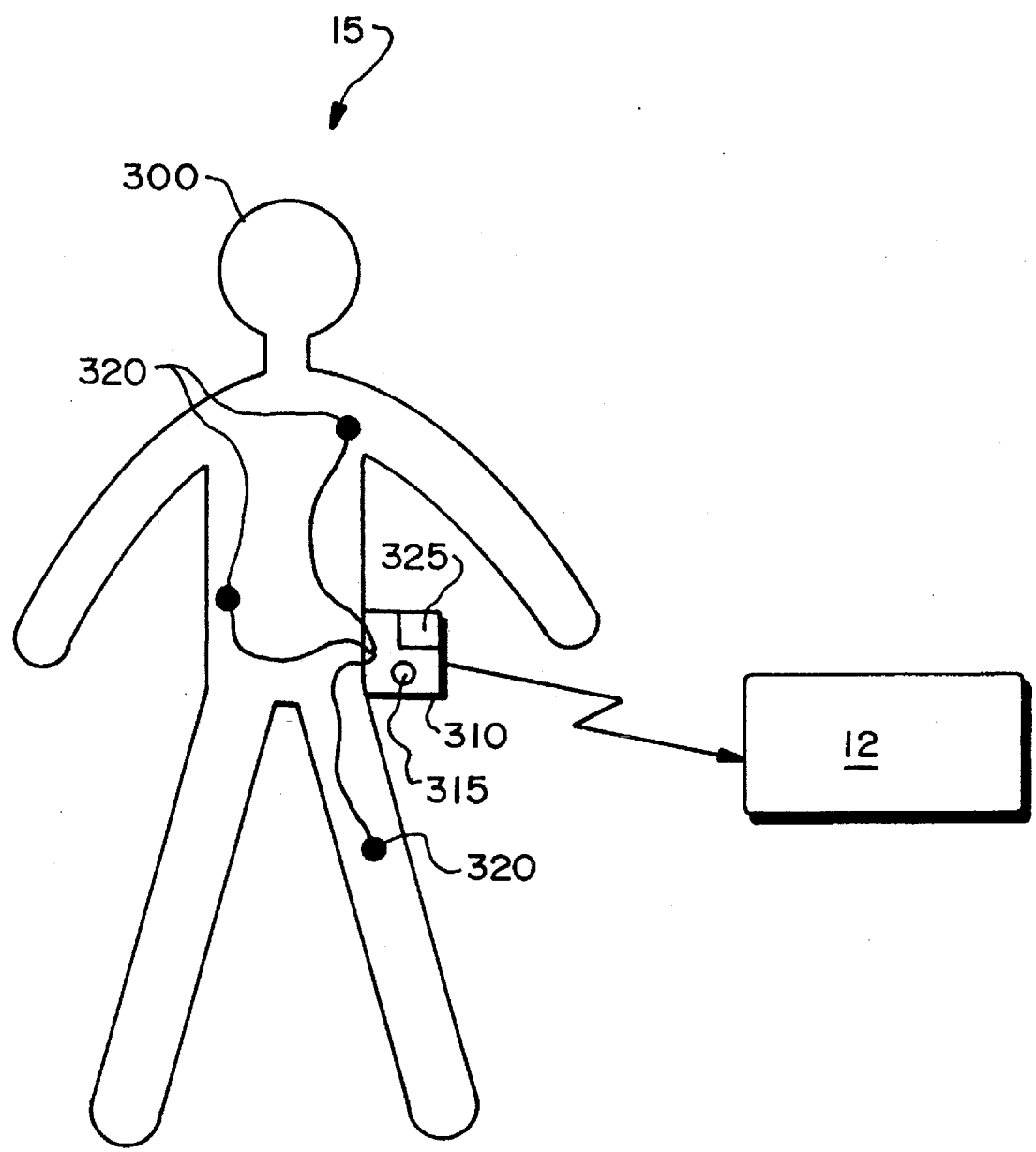
FIG. 3 is a diagram of an ambulatory patient with a conventional telemetry device coupled thereto.

In the exemplary embodiment, the source 15 is an ambulatory patient 300 having a conventional telemetry device 310, as shown in FIG. 3. The telemetry device 310 includes a panic button 315 located on the device, and includes various sensors 320 attached to parts of the patient's body. The sensors may include bioelectrical signal transducers with either direct contact electrodes or indirect contact, e.g., capacitive or magnetic field, electrodes; in addition, the sensors may be physiological transducers, including, but not limited to, photoelectric, optical, accoustic, thermal, mechanical, chemical or radiation sensitive transducers.

The sensors 320 collect body function data, e.g., blood pressure, blood chemistry, heart beat (arrhythmia), either transcutaneously using conventional non-invasive methods or intravenously. The data is assembled as a data packet at the telemetry device 310, which includes a conventional microprocessor and transceiver unit (not shown), and the packet is transmitted to the host computer 12 as patient medical information.

The panic button 315 provides a means for signaling the host computer 12 at the patient's request; this arrangement enables the telemetry device to interact with the host computer in a manner other than the typical methods of providing information, e.g., CSMA/CD or periodic polling of all the sources 15 by the host computer 12. The panic button 315 also provides the patient with a means for acknowledging receipt of a pre-programmed message from the host computer 12 when an alarm condition has been met.

The telemetry device 310 may also include a conventional radio positioning device 325, such as a GPS or Loran, for collecting information pertaining to the geographic location of the ambulatory patient 300. This information is provided to the host computer 12 as patient geodetic information.

Figure 4:
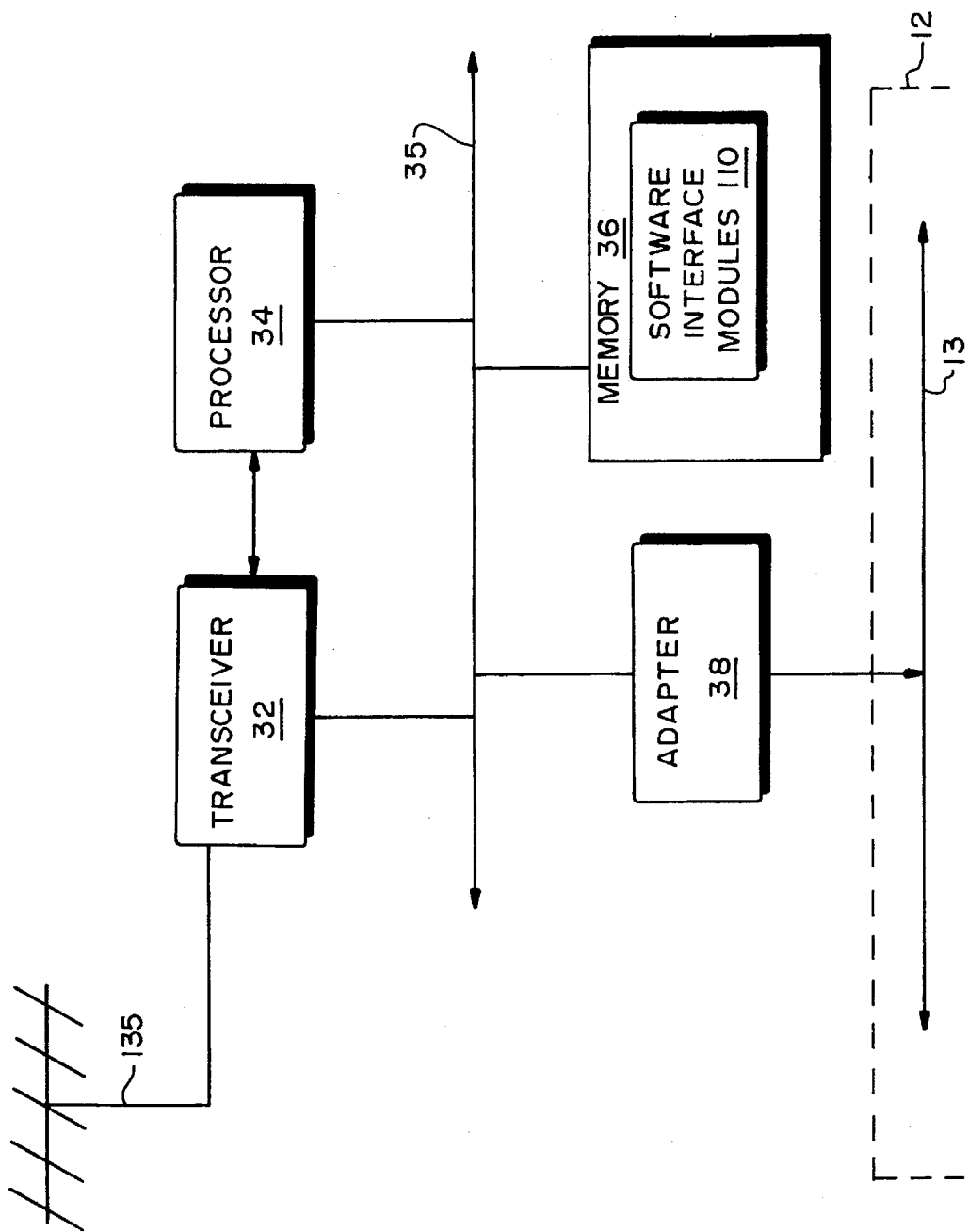
FIG. 4 is a block diagram of a communications system of the host computer.

The communications system 30, shown in FIG. 4, provides a receiver/transmitter interface to the host computer 12. Accordingly, the communications system 30 includes a transceiver unit 32, a processor unit 34 and a memory unit 36 interconnected by a "front-end" bus 35. As noted, the processes of the software modules 110 are typically resident in the memory unit 36 and executed by the processor unit 34 to control the transfer of information between the communications system 30 and the other components of the computer. The transceiver 32 receives information from the sources 15 and transfers the information to the processor 34 for decoding in connection with known decoding algorithms. There, the information is converted to a message format for transfer to the memory 16 through an adapter 38 coupling the front-end bus 35 to the system bus 13 of the host computer 12. The transceiver 32 also receives data packets from the subscribers 20 and forwards them to the processor 34 as described above; in addition, the transceiver may transmit messages to conventional paging services for distribution to the subscribers 20 and to the patients (sources 15).

Communication to the subscribers 20 (and sources 15) from the host computer 12 is effected by equipping each subscriber/source with a receiver, included within the respective transceiver units, that is capable of receiving messages from the host's transmitter, which is included within the transceiver unit 32. The receiver may be a conventional FM radio receiver circuit adapted for non-interactive, limited-bandwith, wireless network communication, e.g., paging speeds of 1.2K bps, with a conventional FM radio transmitter at the host, although other receiver and transmitter arrangements, such as wireless modems, may be used. It is also understood that wide-bandwidth channels may be utilized; however, the method and apparatus described herein reduces the amount of bandwidth needed to accomplish the functions provided by the invention. In accordance with the exemplary embodiment of the invention, each subscriber/source has a radio receiver circuit for receiving paging information from the host 12 and a radio transmitter circuit for transmitting packets of parameter data to the host over wireless media.

Figure 5:
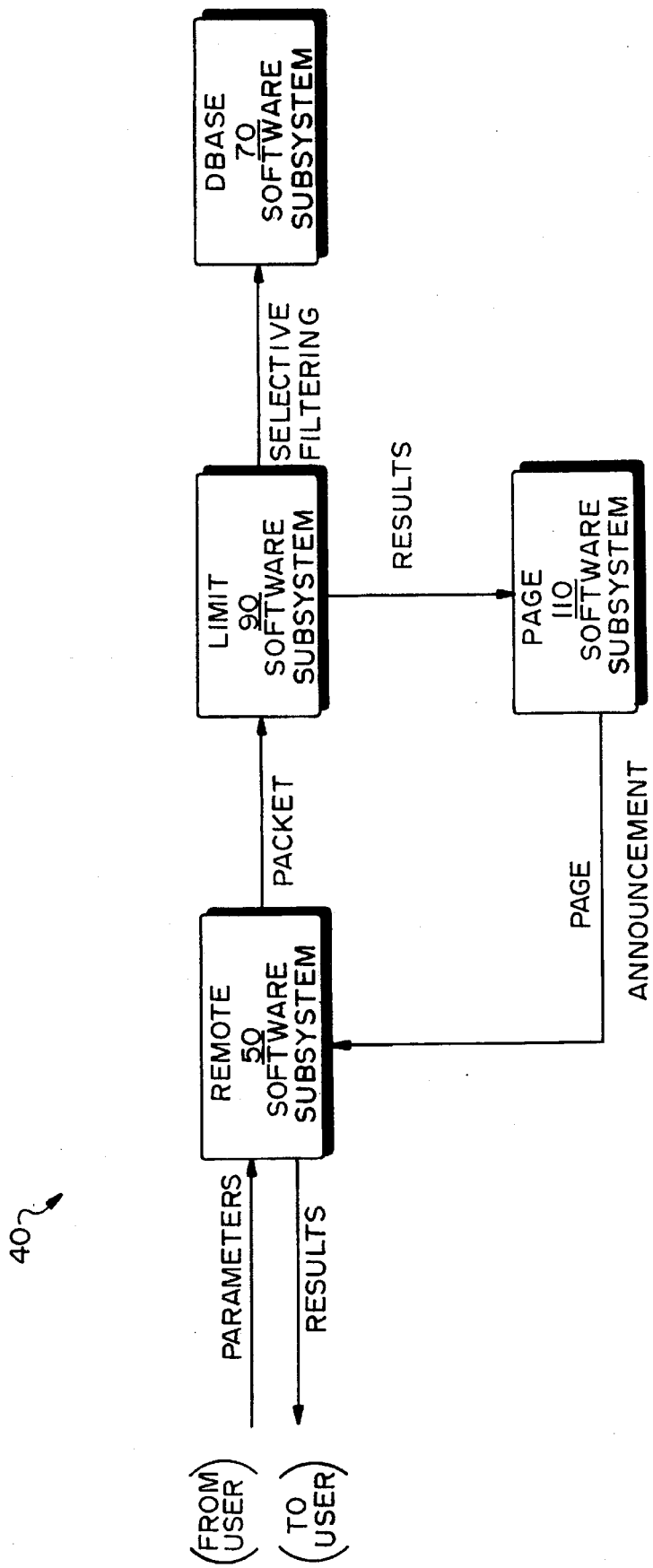
FIG. 5 is a flow diagram of the interaction between a REMOTE software section of the subscriber device, and LIMIT, DBASE and PAGE software sections of a software system of the host computer in accordance with the invention.

One objective of the system according to the invention is to provide fast and efficient access to the information files provided by the sources 15. Another objective is to provide selective filtering of the information in response to selection and associated limit parameters provided by the subscribers 20. To achieve these objectives, the software modules of the subscriber 20 and the host computer 12 are organized as a software system 40 comprising four (4) software subsystems: the remote (REMOTE 50) subsystem, the host (LIMIT 90) subsystem, the database (DBASE 70) subsystem and the transmission (PAGE 110) subsystem. A flow diagram of the interaction between these portions of the software system 40 is illustrated in FIG. 5.

In general, the REMOTE 50 software allows a user to accurately and efficiently enter selection and limit parameters at the subscriber device 20. Further, the REMOTE 50 software organizes the parameters into a data packet format and controls the transfer of the packet to the LIMIT 90 software subsystem over the communications network. The LIMIT 90 software interfaces to the DBASE 70 software subsystem to perform selective filtering of the database information in response to the parameters of the packet. The results of the selective filtering process are then communicated back to the REMOTE 50 software by the PAGE 110 software subsystem, preferably by paging transmission. It should be noted that the DBASE 70 software architecture could be different from that of the LIMIT 90 software; only the interface between these processes need be defined. As described below in connection with FIGS. 11A and 11B, this interface consists of the exchange of messages between the processes.

Each of these subsystems comprise a plurality of independent processes for performing specific operations. Because some of these operations require more time to complete than others, the arrangement of independent processes allows various operations to execute in parallel or to execute on other machines. The processes functionally interconnect through logical path sockets, i.e., virtual circuit connections, which, for the illustrative embodiment described herein, are TCP/IP sockets.

Figure 6:
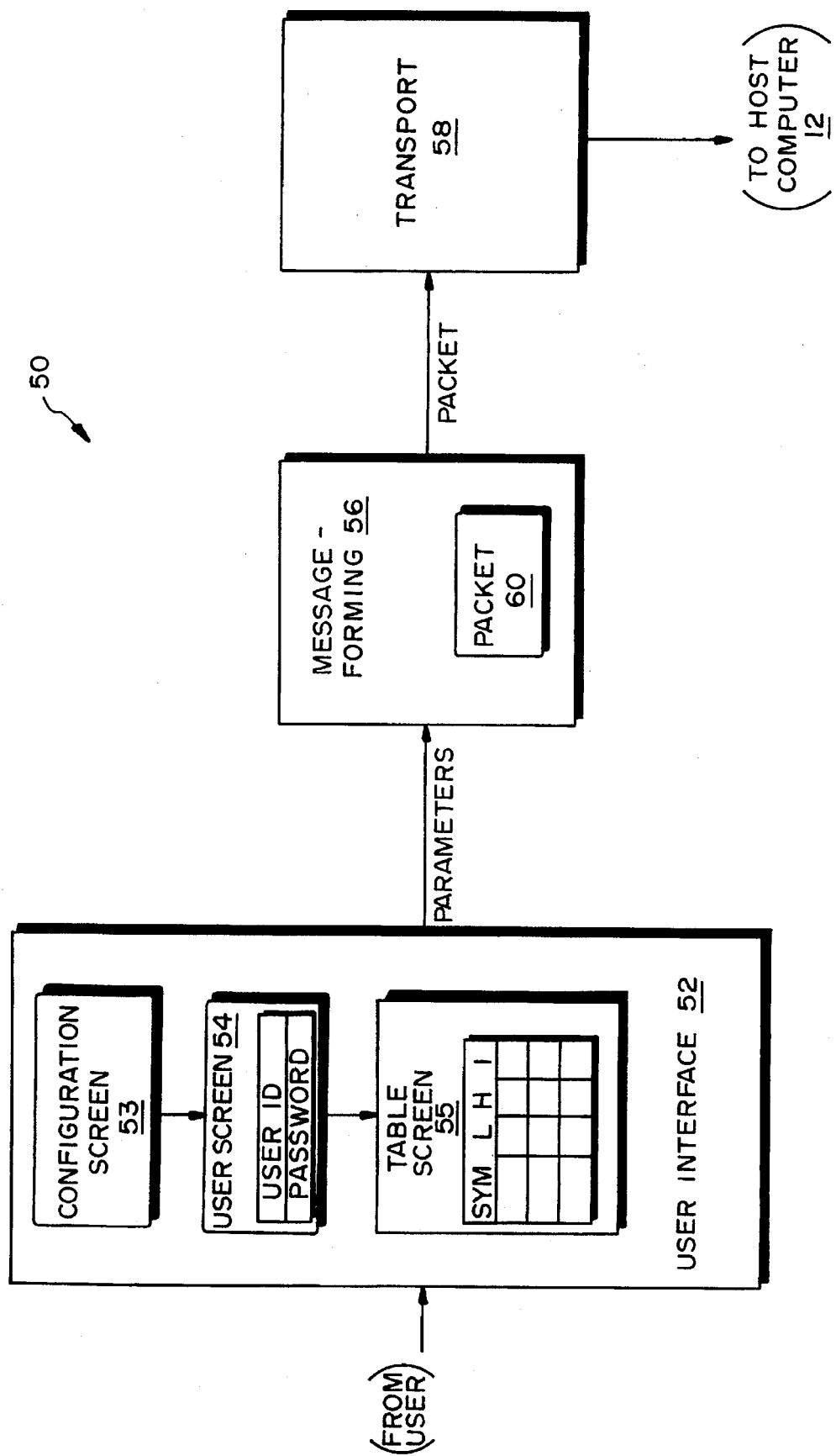
FIG. 6 is a block diagram of the processes constituting the REMOTE software section of FIG. 5.

FIG. 6 illustrates the processes constituting the REMOTE 50 software subsystem. The USER INTERFACE 52 process facilitates configuration of the subscriber device 20 and entry of the limit parameters by providing speech recognition and voice response interface capabilities to an authorized user; however, for the exemplary embodiment set forth herein, the USER INTERFACE 52 provides a series of menus on the display 28 (FIG. 2). Initially, a configuration screen 53 enables selection of a communications port, e.g., a serial port, and inquires about the type of modem connected to that port. A user screen 54 then prompts the authorized user to enter a user identification (ID) and a password. Typically, the user ID comprises a 20-character alpha-numeric string, while the password is an 8-character string. The password provides a measure of security by enabling validation of the user.

A table screen 55 provides a template for entering the selection and limit parameters. The selection parameter is typically a symbol (SYM) specifying, for example, a particular blood chemistry parameter. A dictionary of symbols feature of the interface process allows a user to identify appropriate symbol acronyms and abbreviations. The limit parameters, which are typically numeric characters, include a low (L) or "initial" limit value, a high (H) limit value and an incremental (I) limit value. The USER INTERFACE 52 process validates the format of these parameters but does not interpret them. In the exemplary embodiment of the invention, the incremental limit is used to increment both the initial and high limits by the specified value when either of those latter limits are met, thereby maintaining a limit "window"; accordingly, the limit parameters function as "adaptive" limits. In an alternate embodiment, the incremental limit may specify the relation in degree or number between two similar things, e.g., the rate of change of the blood chemistry parameter from a previous (initial limit) close. Here, the high limit is not needed. Use of the incremental limit as a ratio of change is particularly advantageous in such medical information applications, as described further below.

Figure 7:
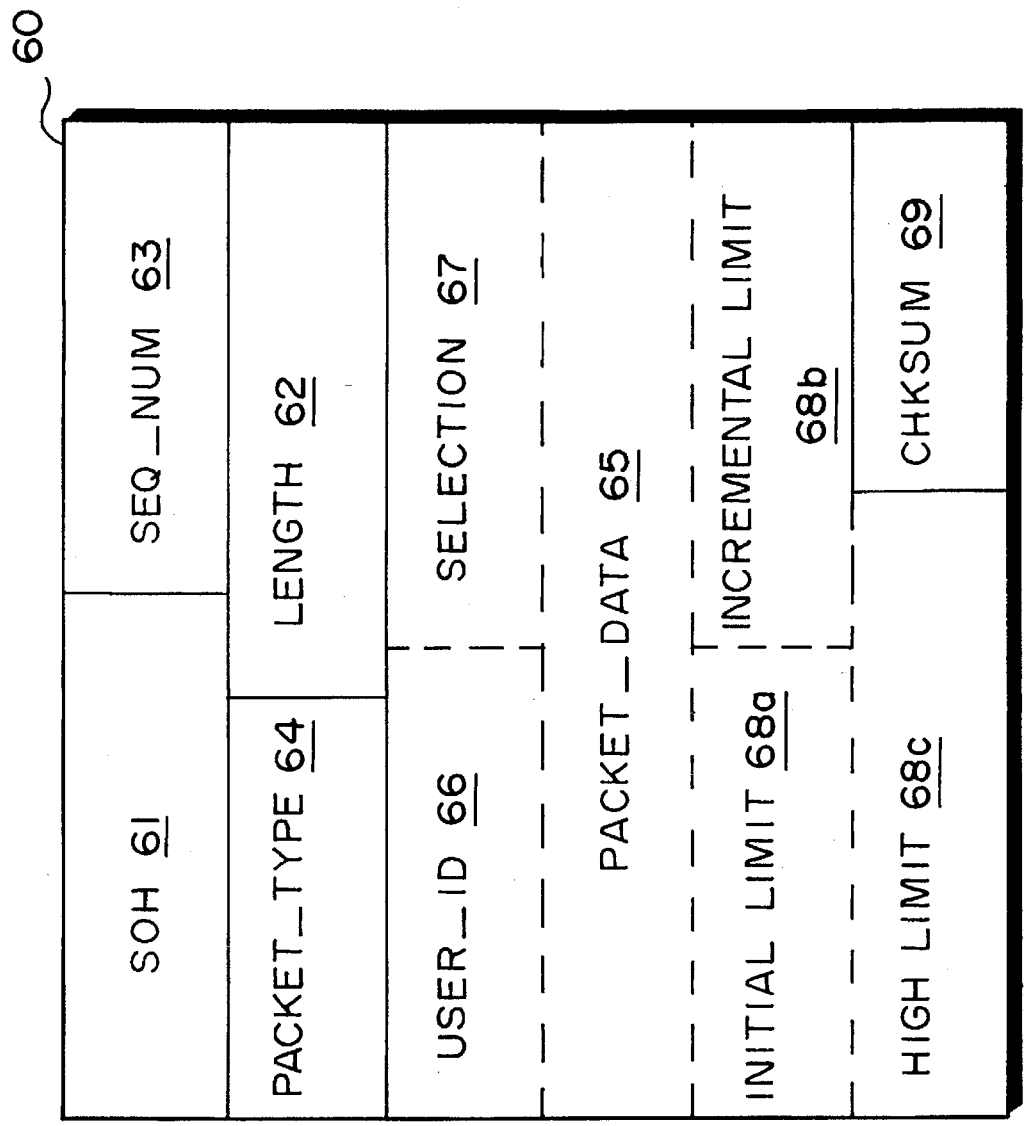
FIG. 7 is a diagram of the format of a data packet used to transfer parameters from a subscriber to the host computer.

A MESSAGE-FORMING 56 process assembles the parameters into a data packet 60 for transfer to the host computer 12. The format 60 of a typical data packet is depicted in FIG. 7. An eight-bit "start-of-header" SOH field 61 identifies the beginning of the packet and a 16-bit LENGTH field 62 identifies the amount of data in the packet. The field SEQ_NUM 63 is an eight-bit packet identification value and the PACKET_TYPE field 64 identifies whether the packet includes command and data parameters or control-type information.

The PACKET_DATA field 65 may be as large as two hundred and fifty-five bytes and consists of subfields that include a user identification USER_ID subfield 66, a selection parameter SELECTION field 67 and limit parameter LIMIT fields 68a–c. Preferably, the SELECTION field 67 contains symbol data and the LIMIT fields 68a–c contain numerical data. Lastly, an eight-bit checksum CHKSUM field 69 consisting of an algebraic sum of transmitted characters is included within the packet for reliability purposes.

Referring again to FIG. 6, the packet 60 is uploaded to the host computer 12 over the communications network 45 in accordance with a conventional asynchronous transfer protocol implemented by the TRANSPORT 58 process. This process initiates a connection to the host, preferably using a conventional wireline modem circuit, thereby obviating the need for a continuous, interactive exchange with the host during the selection and limit entry process.

Figure 8:
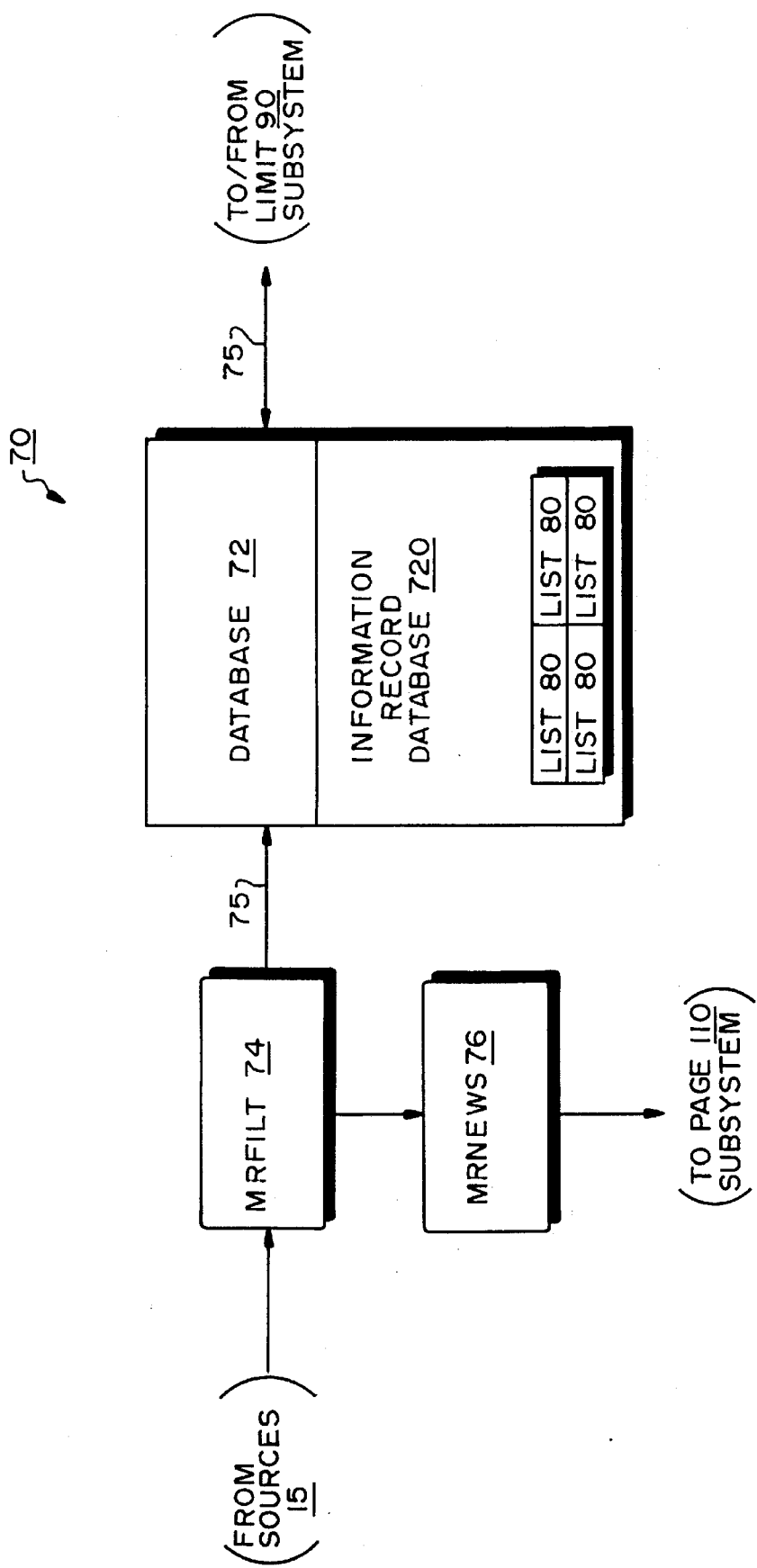
FIG. 8 is a diagram of the processes constituting the DBASE section of FIG. 5.

FIG. 8 depicts the processes constituting the DBASE 70 subsystem. The main DATABASE 72 process is responsible for initializing the MRFILT 74 process of this subsystem and ensuring that it remains active. Because the DBASE 70 software is embodied within the host computer 12 for the exemplary embodiment described herein, DATABASE 52 also initializes the ALERT and BROADCAST processes of the LIMIT 90 subsystem. DATABASE 72 also administers an information record database 720 of information received from the telemetry sources 15. Examples of the administration functions performed by DATABASE 72 include modification of the contents of the information records and transfer of the record contents to other processes upon request. Requests for selected records are effectuated by exchanging messages through direct socket connections 75 with the DATABASE 72 process.

To facilitate the exchange of messages, the processes perform read and write operations to storage locations in memory that are organized to provide data structures, e.g., linked lists. It is to be understood that the CPU 14 performs the actual read, write and booleon operations on behalf of the processes resident in the host memory 16, whereas the communications system 30 incorporates the necessary "intelligence" to perform similar operations on behalf of the processes resident in its memory 36.

Figure 9:
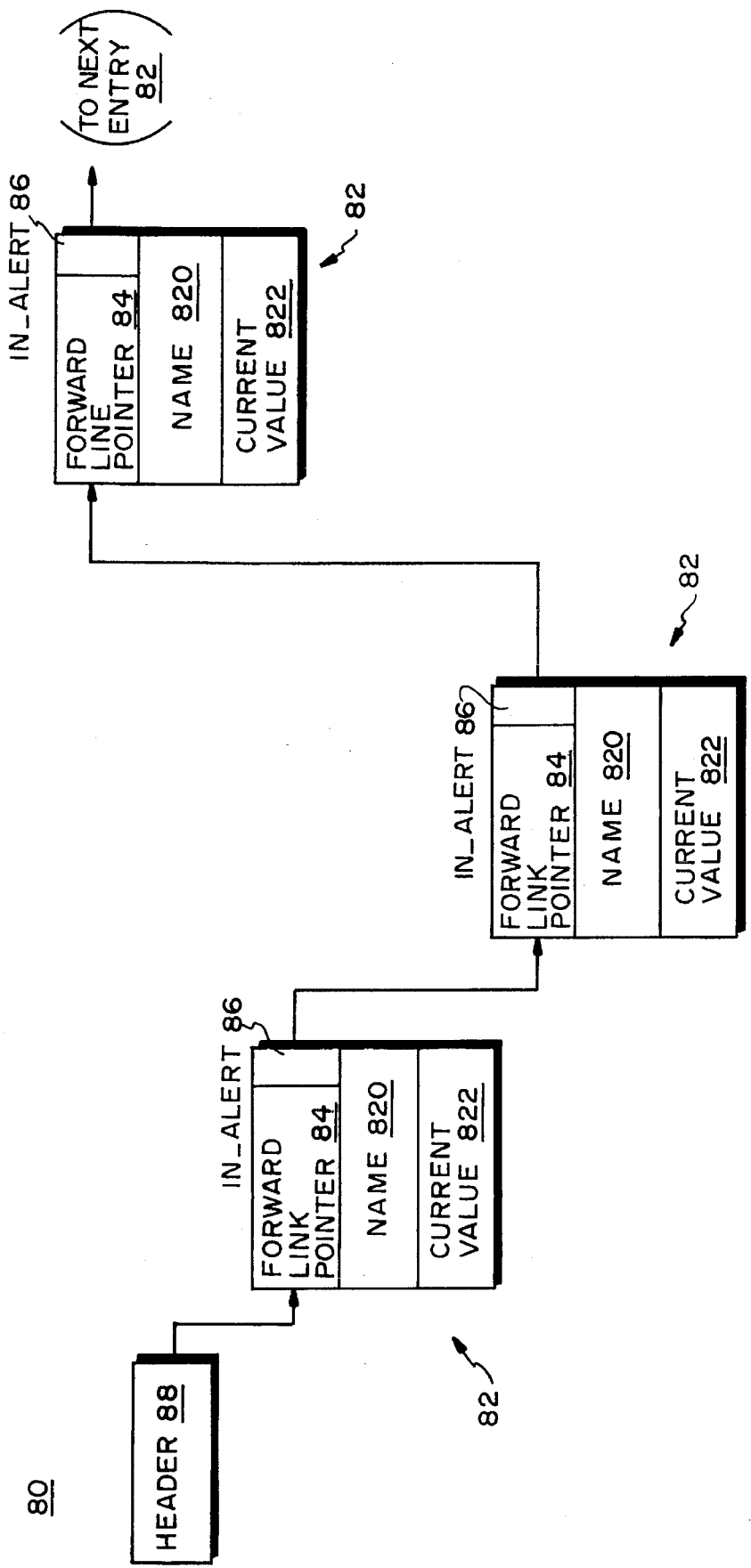
FIG. 9 is a diagram of a linked list data structure including entries for storing information records.

FIG. 9 illustrates a typical linked list 80 that includes entries 82 for storing database records. A header 88 contains an address that points to first entry in the list 80. Each entry 82 contains a forward link pointer 84 referencing the memory location of the next entry in the list; therefore, the entries 82 do not have to occupy consecutive locations in memory and additional entries can be dynamically allocated by the operating system 25. Rather than allocating a separate block of memory locations for each entry, the operating system 25 apportions a block into one hundred (100) entries. The blocks may then be swapped in and out of memory at the appropriate time; in the illustrative embodiment, swapping is performed in accordance with standard UNIX System 5 (page) swapping techniques.

Each record entry 82 also contains, inter alia, a record name (symbol) field 820, a current value field 822 and an IN_ALERT flag 86. The IN_ALERT flag 86 is preferably a 1-bit flag that is constantly checked by the DATABASE 72 process to initiate selective filtering of the database information. When asserted, the flag 86 directs the DATABASE 72 process to write the contents of the record entry 82 as an ALERT_LIMIT message to an ALERT process of the LIMIT 90 subsystem.

Figure 10:
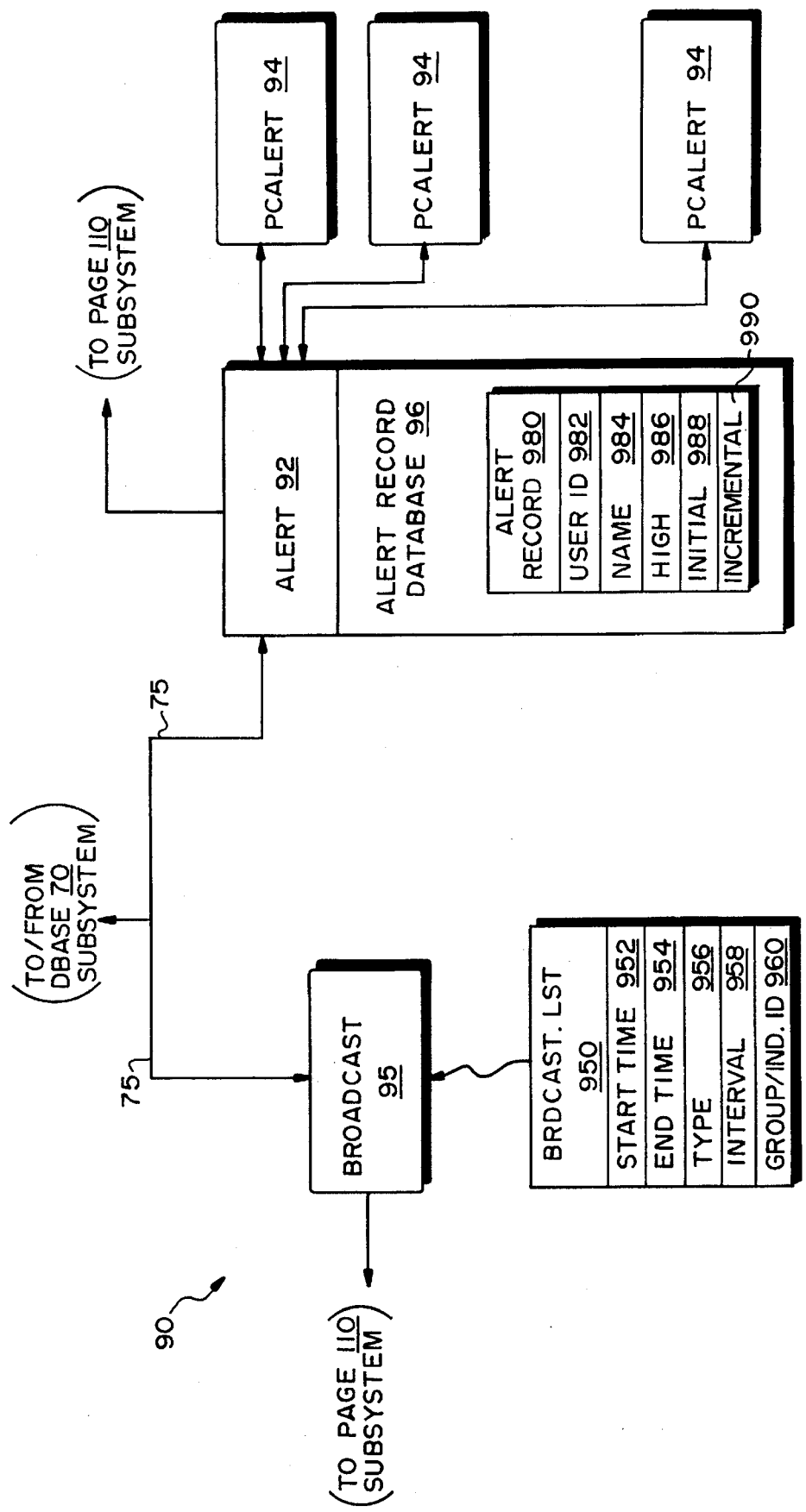
FIG. 10 is a diagram of the processes constituting the LIMIT section of FIG. 5.

FIG. 10 depicts the processes constituting the LIMIT 90 subsystem. The ALERT 92 process is the entity that manages the selection and limit parameters received by the PCALERT 94 processes. The ALERT 92 process maintains its own database 96 of "alert records" 980 which include the parameters provided by the subscribers 20. Specifically, each alert record 980 contains the user ID 982 of the subscriber, the name (symbol) 984 of the selected record, and the high limit 986, initial limit 988 and incremental limit 990 desired for that record. In addition, each record 980 may include a pre-programmed message of instructions for a patient when a limit is met.

When an ALERT_LIMIT message is received from the DATABASE 72 process, ALERT 92 parses the contents of the message and compares the record name field 820 of the message to the name field 984 of the alert record 980. If a match ensues, the parsed current value field 822 of the message is compared to the limits of the matching alert record. If a limit is met, ALERT 92 then sends a page, including the message as described below, to the PAGE 110 subsystem for transmission to the subscriber 20.

The PCALERT 94 process provides an interface between the data packets received from the subscribers 20 and transferred to the ALERT 92 process. PCALERT 94 is preferably distinct from the ALERT process so that the former process can assume responsibility for handling operations required to establish simultaneous connections with subscribers. PCALERT 94 hibernates in a suspended state until prompted by receipt of a packet that either inquires about certain information or requests changes to selection and limit parameters. PCALERT 94 then transitions to a running state and validates the user ID 36 of the packet. Upon validation, the process forwards the packet to the ALERT 92 process.

If the packet involves an inquiry of current limits, the ALERT 92 process obtains the appropriate record from its database 96 and forwards the information back to the PCALERT 94 process. There, the information is transmitted to the subscriber. If the packet includes selection and limit parameters, the ALERT 92 process converts the packet to a message format for transfer to the DATABASE 72 process.

Figure 11A:
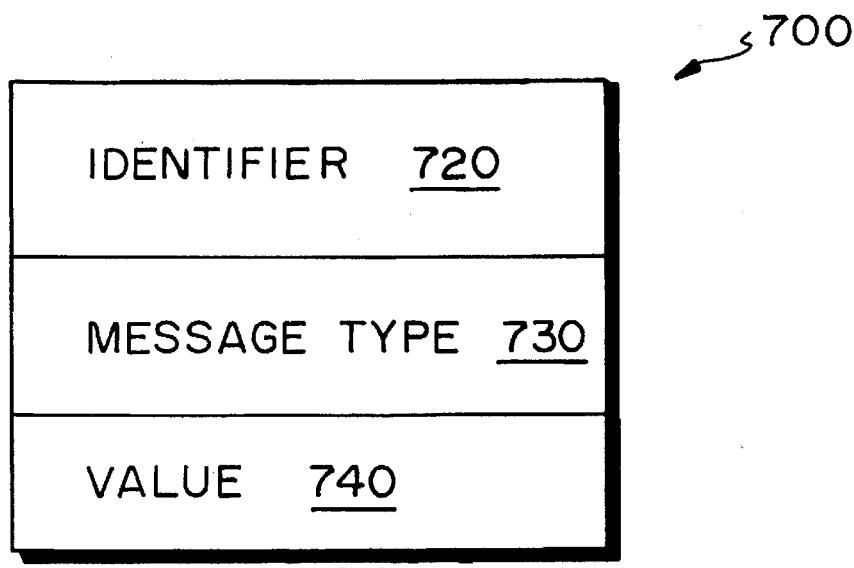
FIGS. 11A and 11B depict the formats of typical messages used for communication among the processes of the system.

As noted, the processes communicate by exchanging messages through socket connections. In accordance with the invention, there are basically two types of messages used in the system: a DB_MSG and a DB_REQUEST. DB_MSG is a 1-way message in the sense that it only directs the receiving process to perform some function. FIG. 11A depicts the format 700 of a typical DB_MSG. The identifier field 720 indicates the symbol (name) of the record. The message type field 730 identifies the action to be taken, such as asserting a flag, and the value field 740 specifies the particular flag, e.g., the IN_ALERT flag 66.

Figure 11B:
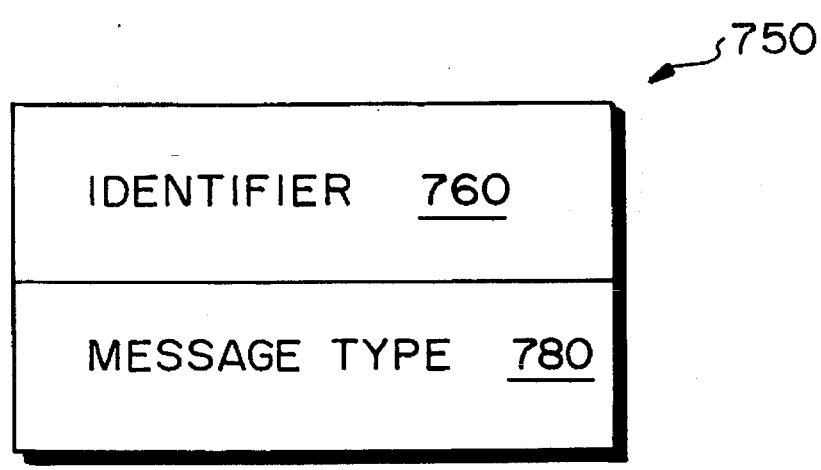

On the other hand, a DB_REQUEST is a request by a process for information; therefore, the process receiving the request is expected to reply. FIG. 11B shows the format 750 of a typical DB_REQUEST, including the identifier field 760 for identifying the name of the record and the message type field 780 for identifying the request, such as the current value of that record entry.

Referring again to FIG. 10, the BROADCAST 95 process manages the type and frequency of announcements that are transmitted for general reception by the subscribers. A broadcast.1st file 950 is created at system initialization and contains a list of group/individual ID records together with broadcast information associated with each record. Specifically, the broadcast information includes the starting time 952 and ending time 954 for broadcasting, the type 956 of announcement to be broadcast, the intervals 958 at which the announcements are broadcast and the group/individuals 960 receiving the broadcast. In some cases, the group ID specifies a class of subscribers for receiving a broadcast.

When a broadcast is scheduled to take place, the BROADCAST 95 process sends a DB_REQUEST 750 to the DATABASE 72 process requesting the contents of a particular record. The information is then forwarded to BROADCAST 95 in a BRDCAST_DATA message. It should be noted that the BRDCAST_DATA and ALERT_LIMIT messages are facsimiles of the record entries 82. Upon receipt of the BRDCAST_DATA message, BROADCAST 95 formats an announcement, establishes a socket connection to the PAGE 110 subsystem and forwards the announcement for broadcast transmission to the subscribers. The BROADCAST 95 process then enters a suspended state and, at the appropriate time, resumes execution.

The MRFILT 74 process, shown in FIG. 8, provides an interface between the sources' information, which is received via data packets having a format similar to that of FIG. 7, and the database subsystem. Specifically, the interface process decodes and converts the received information to DB_MSGs 700 for transfer to the DATABASE 72 process. The MRFILT 74 process also examines the contents of the information feed and, if the examination indicates an appropriate "newsworthy" topic, extracts that information for transfer to the MRNEWS 76 process. This latter process identifies which subscribers, if any, should receive the information, establishes a socket connection to the PAGE 110 subsystem and forwards the information as a page or announcement to that subsystem.

Figure 12:
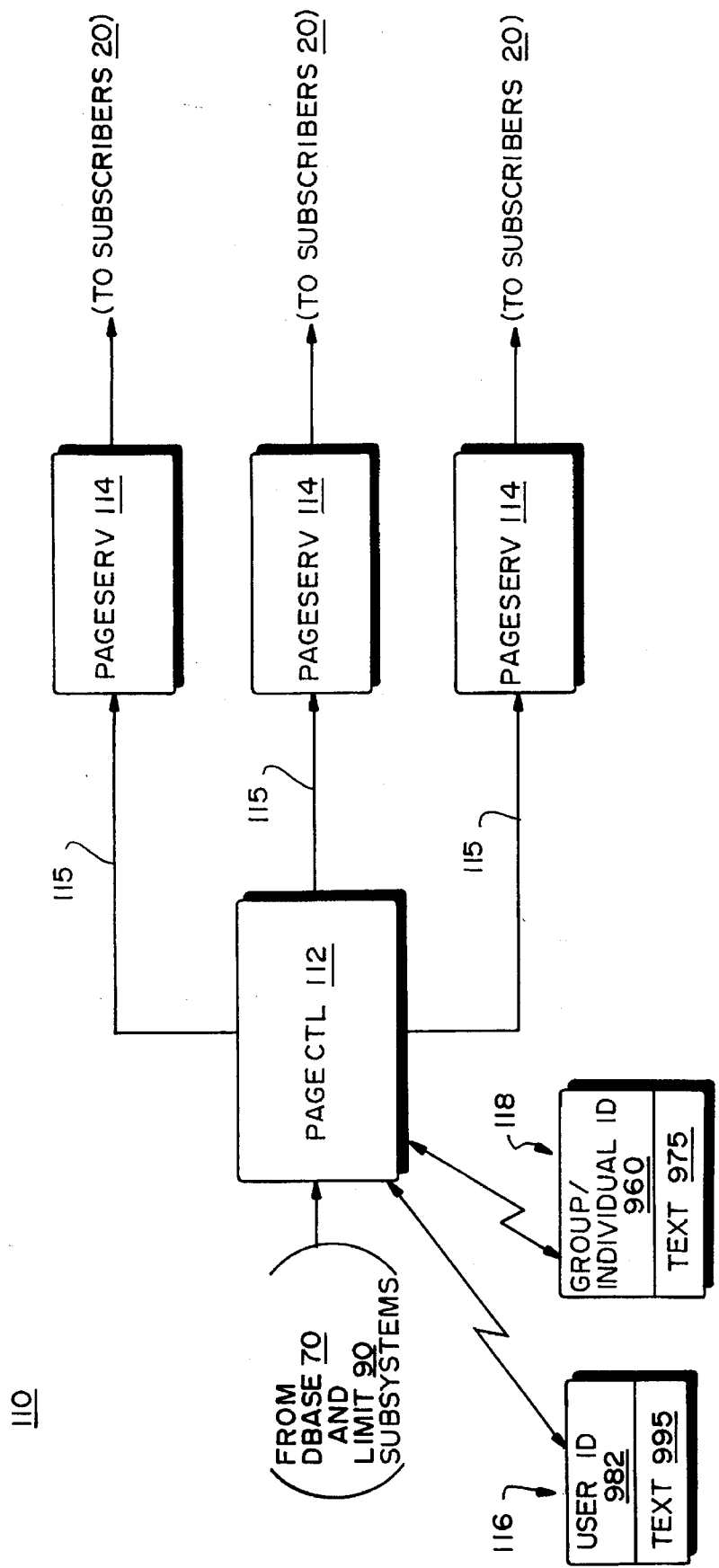
FIG. 12 is a diagram of the processes constituting the PAGE section of FIG. 5.

FIG. 12 depicts the processes constituting the PAGE 110 subsystem. The PAGECTL 112 process manages the interface between the LIMIT 90 and DBASE 70 software, and various known paging services used for distributing messages to the subscribers 20. Specifically, PAGECTL 112 receives pages 116 and announcements 118 from the software processes of the system, and forwards them to available PAGESERV 114 processes. A page 116 includes the ID 982 of a user and a text string message 995, and an annoucement 118 includes a group/individual ID 960 and a text string message 975. The PAGESERV 114 processes operate with the remote paging services by establishing connections with the services. Each PAGESERV 114 process collects the pages 116 and announcements 118 in a queue (not shown) and then transfers them to the paging service for transmission.

Figure 13A:
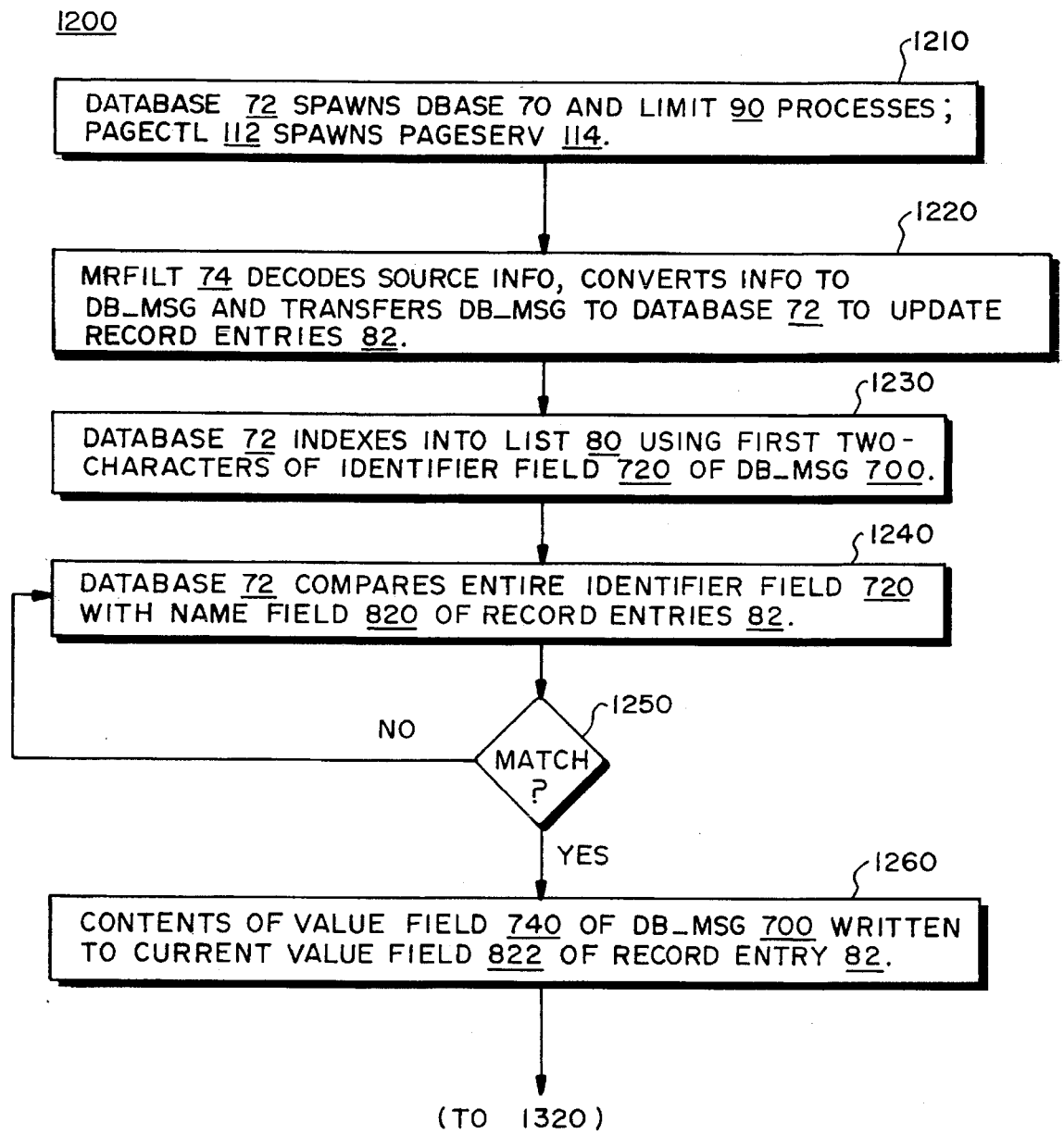
FIGS. 13A, 13B and 13C are flowcharts detailing the sequence for remotely configuring the medical alert distribution system of FIG. 1 in accordance with the invention.
Figure 13B:
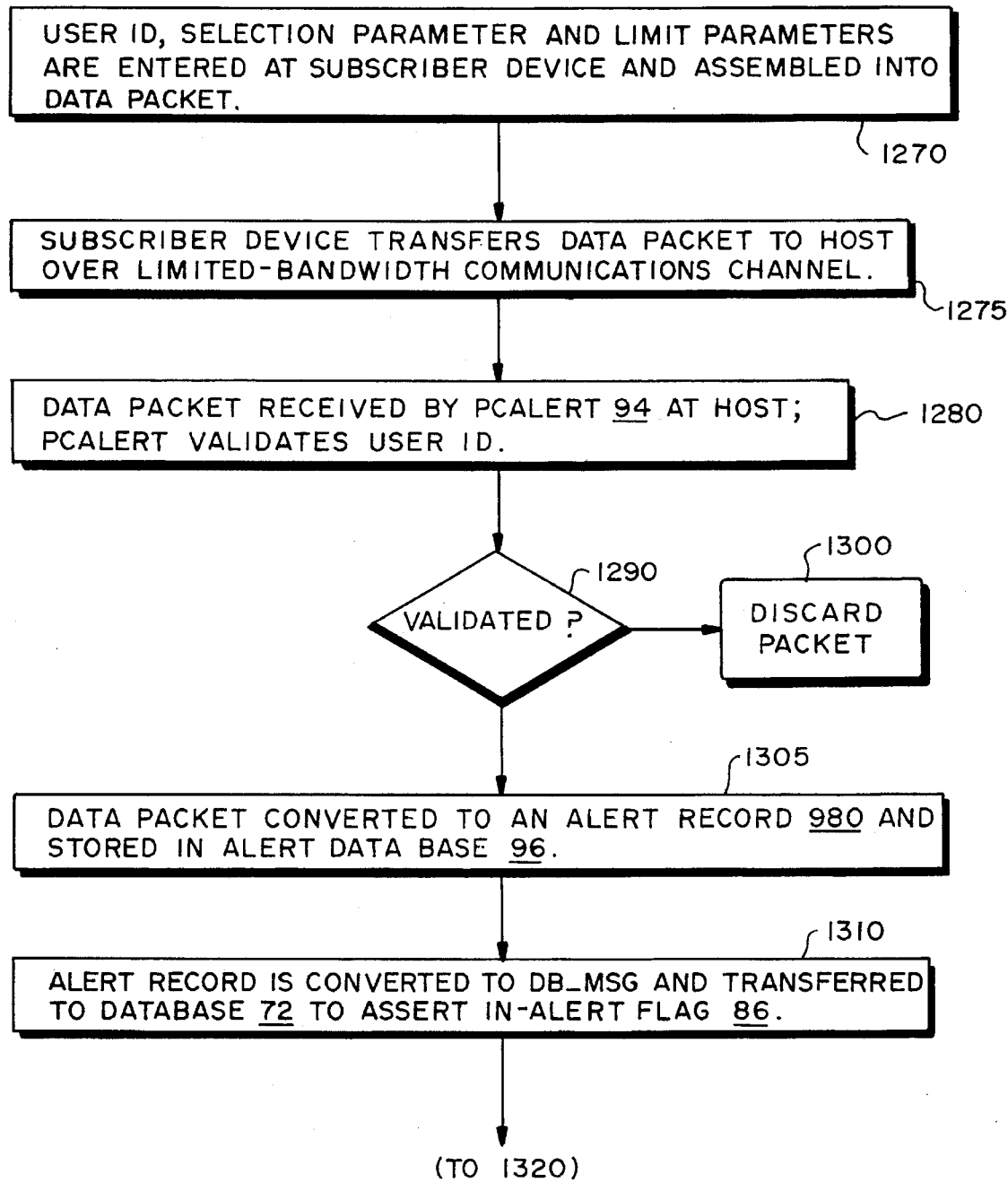
Figure 13C:
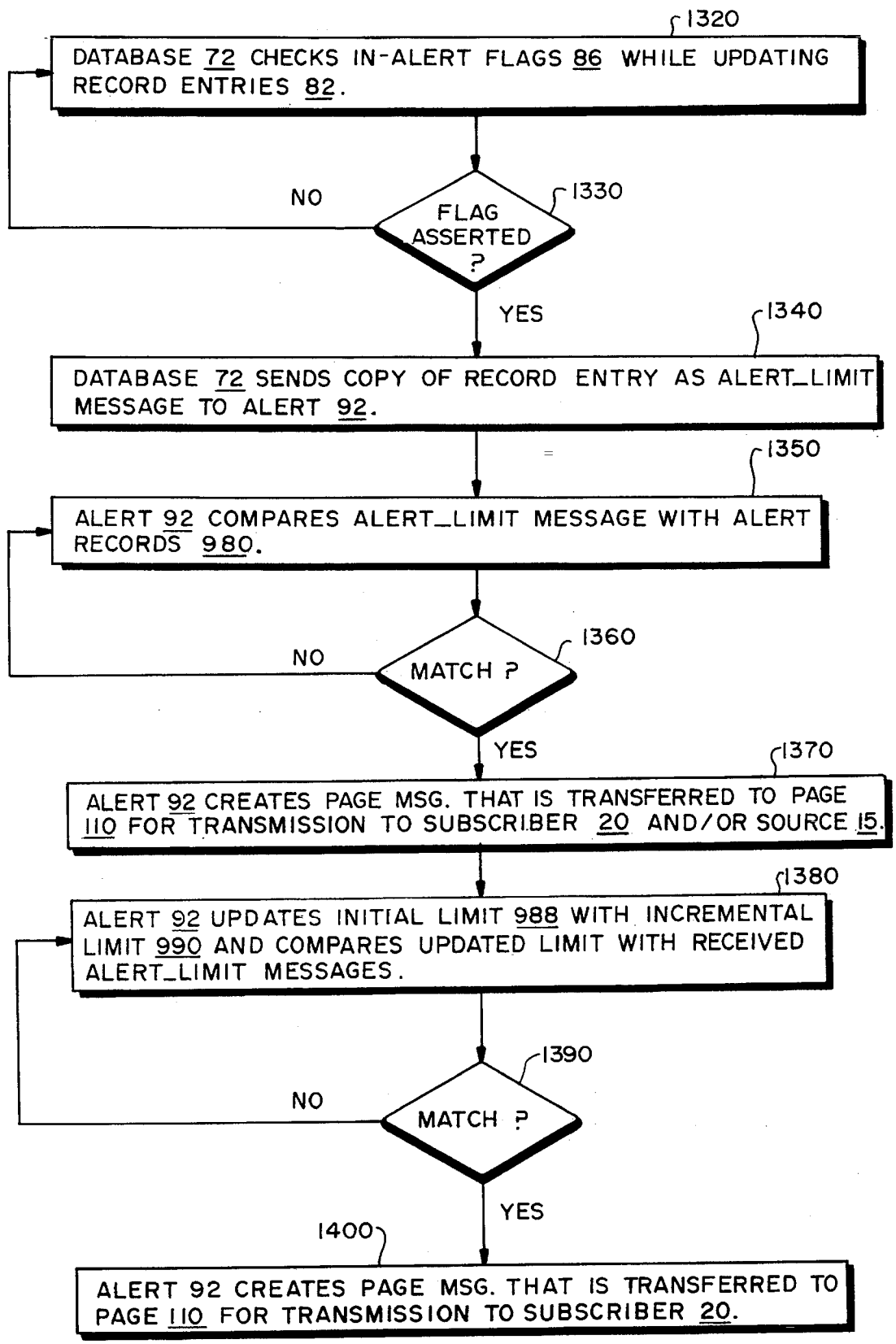

Operation of the medical alert system 10 will now be described in connection with the flowchart 1200 of FIGS. 13A–13C. The system includes at least one subscriber coupled to a host computer that is configured to collect information from telemetry sources attached to ambulatory patients.

At initialization, the DATABASE 72 process spawns the other processes in the DBASE 70 and LIMIT 90 subsystems, fetches groups of the database information files from the storage devices 18 and loads these files into host memory 16. Concurrently, the PAGECTL 112 process spawns PAGESERV 114 processes to communicate with the paging services. (Step 1210.) The DATABASE 72 and PAGECTL 112 processes then scan their respective sockets, waiting for messages.

The MRFILT 74 process decodes streams of incoming information from the telemetry sources, converts them to message formats and transfers the messages to the DATABASE 72 process as DB_MSGs. (Step 1220.)

Upon receiving the DB_MSG, the DATABASE 72 process parses the fields of the DB_MSG and updates the appropriate record entry as follows. The first two characters of the identifier field 720 contained in the DB_MSG are used to identify the correct data structure list 80 in the database 720. (Step 1230.) The DATABASE 72 process then compares the entire identifier field 720 of the DB_MSG with the name field 820 of the record entries 82. (Step 1240.) Preferably, the record entries 82 are stored alphabetically by symbol name. When a match (Step 1250) occurs, the contents of the value field 740 of the DB_MSG 700 are written to the current value field 822 of the record entry 82. (Step 1260.)

At a remote location in relation to the host computer, an authorized user, such as a doctor, may be interested in status of particular body function data, e.g., blood pressure, blood chemistry, heart beats (arrhythmia), of the patient or the location of an ambulatory patient. Additionally, the doctor may be interested in a particular level of the selected data and the rate of change of from that level, or the proximity of travel of the ambulatory patient. Accordingly, the doctor enters a user identification (ID) and a symbol of body function data, i.e., the selection parameter, together with a numerical level value and an adjustment value, i.e., initial and incremental limit parameters, into the subscriber device 20 in response to a menu display; these parameters are assembled into a data packet in accordance with the MESSAGE-FORMING 56 process of the REMOTE 50 software subsystem. (Step 1270.) The data packet is then transmitted to the host computer 12 at the initiative of the subscriber. Arrangement of the parameters to a data packet format is performed at the remote site; therefore, there is no need for a continuous, interactive communication exchange between the subscriber 20 and host 12. (Step 1275.) Upon reception, the host computer responds with an acknowledgement; failure to receive the acknowledgement within a predetermined time interval is an indication that the packet was not correctly received and that retransmission is required.

At the host computer 12, the data packet is received by a PCALERT 94 process associated with a receiver; at this time, the PCALERT 94 process validates the user ID. (Step 1280.) If the user ID is not validated (Step 1290), the packet is discarded. (Step 1300.) If the ID is validated, the packet is forwarded to the ALERT 92 process, where it is converted to an alert record 980 and stored in the alert record database 96. (Step 1305.) The record 980 is then converted to a DB_MSG 700 and transferred to the DATABASE 72 process. (Step 1310.) DATABASE 72 asserts the IN_ALERT flag 86 after indexing into the proper database list 80 as described above. (See Steps 1230–1250.)

Meanwhile, the DATABASE 72 process is constantly checking the IN_ALERT flag 86 of entries 82 while updating their records with incoming DB_MSGs. (Step 1320.) If a flag 86 is not asserted, DATABASE 72 resumes scanning the sockets for incoming messages and updating the appropriate records. (Step 1330.) However, if an IN_ALERT flag is asserted, DATABASE 72 sends a copy of the entire record as an ALERT_LIMIT message to the ALERT 92 process. (Step 1340.) There, the contents of the message are parsed and compared with the limits of the alert records 980. (Step 1350.) If a match (Step 1360) occurs, ALERT 92 creates a page 116 that includes a message specifying that the limit condition was met. The page 116 is transferred to the PAGE 110 subsystem and through to a paging service, where it is transmitted to the subscriber 20 and/or the source 15. (Step 1370.) Upon reception, the subscriber/patient responds with an acknowledgement; again, failure to receive the acknowledgement within a predetermined time interval is an indication that the page was not correctly received and that corrective action, such as retransmission, is required.

The ALERT 92 process then updates the initial parameter 988 of its record 980 with the incremental limit 990 and this latter limit is compared to the contents of subsequently-received ALERT_LIMIT messages. (Step 1380.) When the incremented limit matches the updated value of the stock (Step 1390), the subscriber 20 is again notified in the manner described above. (Step 1400.)

While there has been shown and described an illustrative embodiment for selectively manipulating a medical database "filter" from a remote location in a non-interactive manner, it is to be understood that various other adaptations and modifications may be made within the spirit and scope of the invention. For example, the invention is applicable to financial and news information databases or information stream applications. Similarly, the invention is applicable to medical laboratory applications, as described below.

In one embodiment of the latter application, a hospital database may be the repository for supplying medical laboratory information about patients. The information may include lab test results or patient data that is periodically monitored, e.g., blood chemistry parameters. This information may be collected at the database and forwarded to the host computer for filtering in accordance with controlling parameters entered at the subscriber device by an authorized user, such as a doctor.

For the above applications, the LIMIT (and DBASE) software of the host computer (and database) and the REMOTE software of the subscriber device operate in the manner described above. For patient data information, the doctor may be concerned about, e.g., the rate of change in the blood chemistry parameters. By entering, at the subscriber device, a selection parameter (specifying a blood chemistry value), an initial limit parameter (specifying a previous value of the blood chemistry) and an incremental limit value (specifying a percent change of the previous value), the information distribution system, operating as set forth herein, will notify the doctor when and if the desired change occurs.

The foregoing description has been directed to specific embodiments of this invention. It will be apparent, however, that other variations and modifications may be made to the described embodiments, with the attainment of some or all of their advantages. Therefore, it is the object of the appended claims to cover all such variations and modifications as come within the true spirit and scope of the invention.

What is claimed is:

1. A medical alert distribution system for distributing information messages to an authorized user, said system comprising:

a source of inbound information records, each information record containing a name and a current value;

a host computer coupled to said source, said host computer including (A) a first memory for storing selection and limit parameters, provided by the authorized user from a remote location, as a first database, said limit parameters including an initial limit and an incremental limit;

(B) means for selectively filtering the inbound information records in response to said selection and limit parameters, said means for selectively filtering including first means, for comparing said selection parameter against said information records to determine if a said information record name matches said selection parameter, and for asserting a flag associated with said information record having said name which matches said selection parameter;

second means, coupled to said first means for comparing, for comparing said current value of said information record with said initial limit parameter when said flag associated with said information record is asserted;

means, coupled to said comparing means, for creating a selectively filtered message in response to said matched condition, said selectively filtered message including said current value of the information record; and (C) means for distributing said selectively filtered message to the authorized user.

2. The apparatus of claim 1 wherein said source of inbound information records comprises an inbound stream of information records.

3. The apparatus of claim 1 wherein said source of inbound information records comprises an external database subsystem.

4. The apparatus of claim 1 wherein said source of inbound information records comprises a second memory for storing said inbound information records as a second database.

5. The system of claim 4 further comprising means for managing the information records of said second database, said managing means including means for updating said current value of the information record.

6. The system of claim 5 wherein said managing means comprises a first DATABASE software process executed by a central processing unit of the host computer.

7. The system of claim 6 wherein said comparing means comprises a second ALERT software process executed by said central processing unit.

8. The system of claim 7 wherein said selectively filtered message is a paging message.

9. The system of claim 8 wherein said distributing means is a communications system comprising a memory means for storing a third software process and a processor means for executing said third software process to control the transfer of said paging message to the authorized user.

10. The system of claim 9 further comprising:

means, coupled to said comparing means, for incrementing said initial limit with said incremental limit parameter.

11. The system of claim 10 wherein said incrementing means comprises said ALERT process executed by said central processing unit.

12. A method for distributing medical information messages to authorized users in response to selection and limit parameters provided by the authorized users, said method comprising the steps of:

storing medical information records received from an incoming source of records as database entries, each database entry having as contents a name, a current value and a flag;

receiving said selection and limit parameters as alert records, said selection parameter comprising the name of a selected database entry and said limit parameters comprising an initial limit value and a high limit value;

asserting said flag of said selected database entry in response to said selection parameter matching the name of said selected database entry;

updating the contents of said selected database entry in accordance with the received medical information records;

comparing the updated contents of said selected database entry with said limit parameters; and creating a medical information message in response to the updated contents of said selected database entry exceeding one of said limit parameters, and transmitting said medical information message to the authorized users.

13. A medical alert distribution system for distributing medical information messages to authorized users in response to selection and limit parameters provided by the authorized users, said system comprising:

- a database for storing medical information records received from an incoming source of medical information records as database entries, each database entry having as contents a name, a current value and a flag;
- means for receiving said selection and limit parameters as alert records, said selection parameter comprising the name of a selected database entry and said limit parameters comprising an initial limit value and a high limit value;
- means, coupled to said receiving means, for asserting said flag of said selected database entry in response to said selection parameter matching the name of said selected database entry;
- means, coupled to said database, for updating the contents of said selected database entry in accordance with the received medical information records;
- means for comparing said curent value of said selected database entry with said limit parameters; and
- means for creating a medical information message in response to current value of said selected database entry exceeding one of said initial limit value and said high limit value to enable distribution of said medical information message to the authorized users.

* * * * *